United States Patent [19]
Walles

[11] Patent Number: 5,233,081
[45] Date of Patent: Aug. 3, 1993

[54] METHOD FOR SULFONATION USING POROUS ABSORBER MATERIAL

[76] Inventor: Wilhelm E. Walles, 6648 N. River, Freeland, Mich. 48623

[21] Appl. No.: 859,846

[22] Filed: Mar. 30, 1992

[51] Int. Cl.$^5$ ............... C07B 45/02; C07C 303/06
[52] U.S. Cl. ............... 562/75; 525/344; 562/33; 562/39; 562/95; 558/41; 558/42
[58] Field of Search ............... 562/33, 39, 75, 95; 558/41, 42; 525/344

[56] References Cited

U.S. PATENT DOCUMENTS

| | | | |
|---|---|---|---|
| 3,620,684 | 11/1971 | Brooks | 422/193 |
| 4,111,438 | 9/1978 | Longfoot | 422/193 |
| 4,226,796 | 10/1980 | Akred | 558/41 |
| 4,261,916 | 4/1981 | Crosby | 558/33 |
| 4,902,493 | 2/1990 | Walle et al. | 423/522 |
| 4,915,912 | 4/1990 | Walle et al. | 422/160 |

Primary Examiner—Bernard Dentz
Attorney, Agent, or Firm—Lynn E. Cargill

[57] ABSTRACT

A method for preparing a sulfonated compound with minimal or no waste products using a porous inorganic material absorber. The absorber is saturated with a compound to be sulfonated and then contacted with a sulfonating gas mixture to form a sulfonated product. After forming the sulfonated product, excess sulfonating gas is removed by contacting the sulfonated product with warm air. The sulfonated product is then neutralized and the product is removed with water from the inorganic material absorber. The absorber is then dried with hot air so that it may be reused for future sulfonation processes. The process results in preparation of a sulfonated compound having inorganic salts present in an amount less than about 1.0 percent by weight based on total sulfonated product weight. The process results in highly effective sulfonation of a compound with formation of little or no waste materials, particularly waste materials such as solvents and undesirable inorganic salts. Also disclosed is the resulting sulfonated product.

17 Claims, 2 Drawing Sheets

METHOD FOR SULFONATION USING POROUS ABSORBER MATERIAL

TECHNICAL FIELD

This invention relates generally to a sulfonation method, but more particularly relates to a sulfonation method which reacts gaseous $SO_3$ with the compound to be sulfonated on a porous inorganic material absorber and the resulting product.

BACKGROUND OF THE INVENTION

Traditionally, methods for sulfonation of hydrocarbon compounds have included the use of fuming sulfuric acid and liquid or gaseous $SO_3$. Sulfonation is usually carried out in either film or free annular jet reactors.

Sulfonation methods using these types of reactors have been problematic for several reasons. First, the high viscosity of the sulfonation reaction product interferes with the sulfonation of remaining unreacted feedstock, and results in lowered yields of final sulfonated reaction product. Secondly, the high viscosity of the sulfonated reaction product requires the use of scrapers and/or solvents to keep the sulfonated product moving through the reactor. An example of a method for sulfonation using a thin film reactor is set forth in U.S. Pat. No. 3,620,684 to Brooks. This patent discloses an improved method for the sulfonation of organic reactant by means of a reaction between a liquid organic reagent and sulfur trioxide vapor in a thin film reactor. An example of a method of sulfonation using a jet reactor is set forth in U.S. Pat. No. 4,111,438 to Brooks.

Other prior art methods have included the use of $SO_3$ or $H_2SO_4$ for sulfonation. These methods also present problems. One such problem arising from the use of $SO_2$ is that $SO_2$ is a gas at room temperature and consequently requires a pressurized or cold reactor. This adds to the cost of manufacturing. The use of $H_2SO_4$ results in contaminated end product, thus requiring additional steps for recovering the product. For example, the use of $H_2SO_4$ results in large quantities of inorganic salts present in both the end product and the waste water. The inorganic salts are undesirable because when the sulfonated product is used in emulsified products such as hand creams, liquid detergents, liquid soap and shampoos, the inorganic salts cause phase separation and result in unusable products.

Various other references teach the sulfonation of organic feedstocks in recycle loop reactors. Examples of these are set forth in U.S. Pat. No. 4,226,796 to Akred and U.S. Pat. No. 4,261,916 to Crosby. The Akred patent teaches the use of sulfur trioxide as a sulfonating agent in a recycle loop reactor where the feedstock is diluted with its recycled sulfonation product. To moderate the effects of the heat of reaction, Akred teaches that in some instances it is necessary to use a solvent, such as carbon tetrachloride, when the reaction product has a high melting point or is highly viscous. Also, in this type of reaction there is significant heat evolved due to the reaction necessitating the use of heat exchangers to remove excess heat.

The Crosby patent discloses a design for a turbulent flow plate mixer for mixing at least two fluids in the recycle loop reactor. This patent discusses that significant heat of reaction is produced during sulfonation with sulfur trioxide. To moderate the effects of the heat of reaction, Crosby states that it may be necessary to dilute the sulfur trioxide with a diluent such as a chlorinated hydrocarbon, which may be undesirable. The prior art methods disclosed in Akred and Crosby are undesirable because they utilize solvents that are difficult to dispose of, such as chlorinated aliphatic hydrocarbons (e.g. carbon tetrachloride and $MeCl_2$) and fluorocarbons. The solvents result in contaminated end products, and are toxic, carcinogenic and adversely effect the environment.

Unlike the prior art methods mentioned above, the process of the present invention utilizes recycled $SO_3$ gas obtained from a sulfonator recycler to sulfonate compounds which have been saturated into a porous inorganic material absorber. The recycling of $SO_3$ gas for this purpose is described in U.S. Pat. Nos. 4,902,493 and 4,915,912, which are hereby incorporated by reference.

Porous inorganic material absorbers have been used in the past in some other reactions. Clay is such an absorber and has been used to heat and vaporize reactants and as a filter. However, the patents disclosed herein do not use clay as a reaction media. U.S. Pat. No. 2,448,184 to Lemmon teaches the use of fluidized clay to remove sulfuric acid after sulfonating a hydrocarbon in a sulfonation reactor with sulfuric acid. The sulfonated hydrocarbon is removed from the reactor and then contacted with adsorption clay to remove the sulfuric acid.

U.S. Pat. No. 2,654,658 to Marshall teaches the nitration of organic compounds by contacting a dense bed of heated, finely divided, suspended solids with nitric acid. The heated solids cause the nitric acid to vaporize and contact the vapors of organic compounds to be nitrated.

Upon reading these patents, it can be seen that the Lemmon and Marshall references do not teach the use of a fluidized clay as a media on which reaction actually occurs. Lemmon uses the clay only as a filter. Marshall uses a fine solid media only for heating and vaporizing a reactant.

Therefore, it is the primary object of the present invention to provide a method for sulfonating a compound which employs a reusable porous inorganic material absorber as a media on which the sulfonation reaction occurs.

It is a further object of the invention to provide a method for sulfonation which results in a sulfonated product containing less than 10 percent by weight inorganic salts, based on total sulfonated product weight. It is yet a further object of the present invention to provide a sulfonation method which reduces the maximum process temperature of the reaction. It is yet still a further object of the present invention to use $SO_3$ gas obtained from a sulfonator-recycler in the present sulfonation process. It is still a further object of the present invention to provide a sulfonated product containing less than 1.0 percent by weight inorganic salts based on total sulfonated product weight, by the disclosed method.

SUMMARY OF THE INVENTION

In accordance with preferred embodiments of the invention, these and other objects and advantages are addressed as follows.

A method for preparing a sulfonated compound on a porous inorganic material absorber which produces little or no waste products generally includes the following steps. First, a porous inorganic material absorber is contacted with the compound which is to be sulfonated to form an adsorbate. The compounds to be sulfonated include hydrocarbons, aromatic hydrocarbons, alkylated aromatic hydrocarbons, alkylated diphenyloxides, alkanols, amines, imines, polystyrene and other polymers. The adsorbate is then contacted with a gas mixture containing $SO_3$ gas, preferably a mixture including $SO_3$ gas along with a gas inert to reaction with $SO_3$, to form a sulfonated product. The product generally contains sulfonic acid products which may be neutralized and then removed from the inorganic material absorber. Thereafter, the absorber is dried and is available for reuse in future sulfonation reactions. This method has been found to be particularly useful for producing sulfonated alkylated diphenyloxides for use as anionic surfactants.

In summary, this method avoids the problems of undesirably high process temperatures and highly viscous reaction products which consequently interfere with the sulfonation of the remaining reactants. The present method substantially reduces the maximum process temperature of the reaction. Due to the use of the porous absorber reaction media, heat is dissipated, rather than being concentrated in the reactants. Reduced maximum processing temperatures result in a more desirable product.

The method of the present invention does not require the use of solvents to lower the viscosity of the sulfonated product or to moderate the heat of the sulfonation reaction, which result in the production of often harmful waste products and byproducts. Cost savings result since because the byproducts do not have to be separated from the reaction product, and disposal of toxic solvents is not a problem. The present method is designed to be useful in conjunction with a sulfonation recycler, as described in the prior art discussed hereinabove, which results in further cost savings. In addition, the porous absorber reaction media is reusable, a feature which results in cost savings in the sulfonation process.

By practicing the method of the present invention, sulfonated compounds containing inorganic salts in an amount of less than 1.0 percent by weight based on total weight of the sulfonated compounds may be achieved. In many cases, the present method is effective to form sulfonated compounds containing inorganic salts in an amount of less than 0.10 percent by weight based on total weight of the sulfonated compound.

BRIEF DESCRIPTION OF THE DRAWINGS

The nature and extent of the present invention will be clear from the following detailed description of the particular embodiments thereof, taken in conjunction with the appendant drawings, in which.

DETAILED DESCRIPTION OF THE INVENTION

The sulfonated product of the present invention may be prepared on a porous inorganic material absorber in either: (1) a batch reactor where the porous material stays in place in a single compartment of the reactor or (2) in a continuous reactor, where the porous material circulates to various compartments in the reactor. These reactions may be classified as batch reactions and continuous reactions, respectively.

I. Method for Batch Sulfonation

Figure 1:
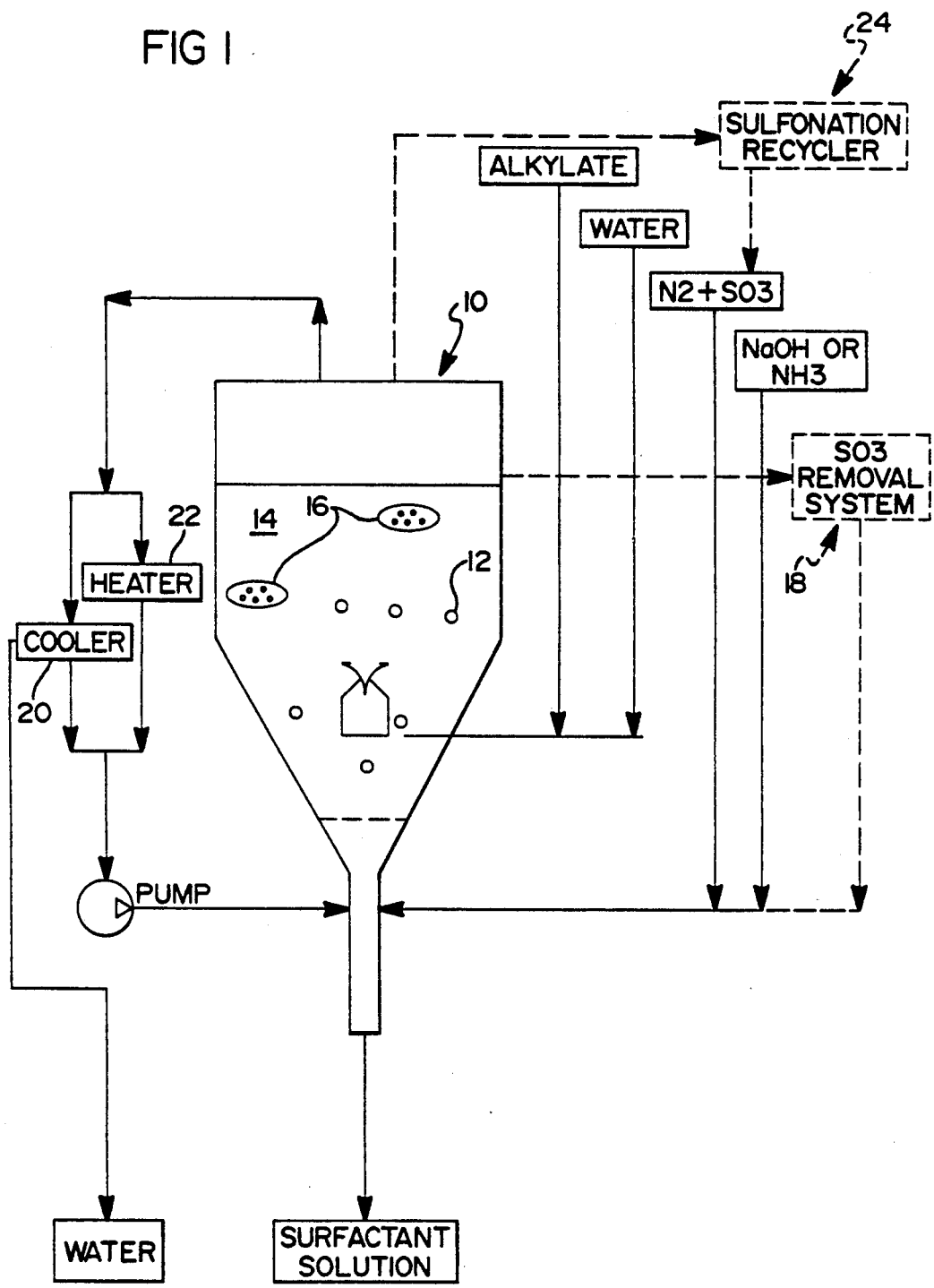
FIG. 1 shows a schematic diagram of the sulfonation process utilizing a porous inorganic material absorber in a batch reactor wherein the absorber is stationary in the reactor.

Referring first to the schematic diagram of FIG. 1, a batch reactor for carrying out the batch method is generally denoted by the numeral 10. In this method for preparing a sulfonated product in batch reactor 10, porous inorganic material absorber 12 remains stationary in one location during the sulfonation reaction. This batch method includes steps as described hereinbelow. The specific reaction illustrated involves sulfonation of an alkylate.

The first step in the batch sulfonation process is contacting the porous inorganic material absorber 12 with the compound to be sulfonated 14. The compound to be sulfonated is generally applied to the absorber in liquid form, to form an adsorbate 16. Next, the adsorbate is reacted with a sulfonating gas mixture. The preferred sulfonating gas mixture includes $SO_3$ gas along with a gas inert to reaction with the $SO_3$ gas, to form a sulfonated product. The sulfonating gas mixture may be $SO_3$, or it may be a gas mixture which includes $SO_3$ gas in combination, preferably, with nitrogen gas or other gases which are inert to the $SO_3$ gas. Other possible $SO_3$ inert gases include dry air, nitrogen, argon, $CO_2$ and $SO_2$.

During or after the adsorbate reaction with the sulfonating gas mixture, the reaction products are cooled or kept to a temperature of about 20° C. by circulating gases or parts of them which are cooled in a cooling chamber 20. In this method, the reaction products are cooled in situ, although any known method of cooling may be feasible. It is also possible to remove the product for cooling at a remote location. Excess sulfonating gas is removed by contacting the sulfonated product with dry air at temperatures of up to about 80° C. by circulating heated air which was heated in a heating chamber 22. The excess sulfonating gas is recovered and recycled during the sulfonation process by a sulfonation recycler shown at 24 for use in subsequent sulfonation reactions. Such sulfonation recyclers have been taught in U.S. Pat. Nos. 4,902,493 and 4,915,912, disclosed above, which have been incorporated by reference.

Any excess unsulfonated compound is removed by a steam distillation process either in reactor 10 or in a separate dryer. Such steam distillation is well known in the art. Although the steam distillation is not the patentable portion of this invention, one of ordinary skill in the art would be able to incorporate such a steam distillation apparatus into the present invention.

Following sulfonation, the acids which were formed in the sulfonated product during the sulfonation process are neutralized by admixing the product with an aqueous base solution of a neutralizing agent selected from the group consisting of the hydroxides, carbonates, acetates and corresponding salts of Li, Na, K, Ca, Ba, Zn, Mg, Al and similar metals or, in the alternative, by contacting the sulfonated product with a neutralizing gas mixture, preferably including $NH_3$ gas. Also, other neutralizing gas mixtures may be utilized which include $NH_3$ in combination with a gas which is inert to $NH_3$. Such inert gases may include air, nitrogen and argon. In that case, $NH_3$ is utilized in an amount between about 5 and about 95 percent by volume based on total volume of the neutralizing gas mixture. Preferably the $NH_3$ gas is present in an amount between about 5 and about 10 percent by volume based on total volume of the neutralizing gas mixture. In the batch reactor 10, the sulfonated product is simultaneously removed from the porous absorber during the neutralization process by known techniques of water extraction. After the water extraction of the sulfonated product, the absorber is dried with hot air which has been heated in heating chamber 22 to a temperature of about 150° C.

Alternatively, when $NH_3$ gas is used in the neutralization process, excess $NH_3$ gas is removed by heating the neutralized sulfonated product with circulating hot air, which has been heated in heating chamber 22 to a temperature of up to about 80° C., followed by air flushing to purge the chamber of excess $NH_3$ gas. The neutralized product is then removed by water extraction and the absorber is dried with hot air as described above. Thereafter, the dried absorber material is cooled with air which has been cooled in cooling chamber 22. This places the absorber in a condition such that it may be reused in future sulfonation processes.

Figure 2:
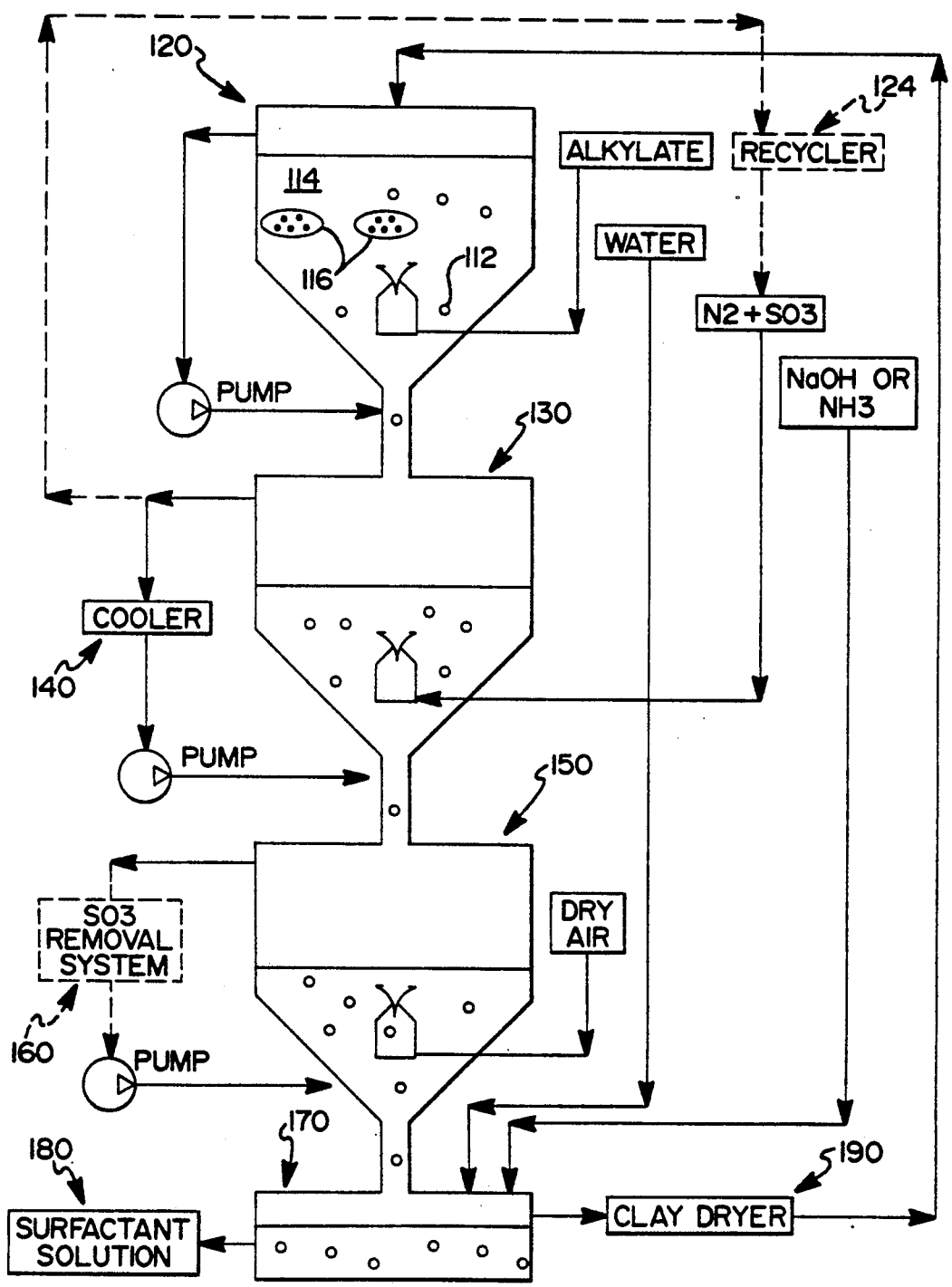
FIG. 2 illustrates the sulfonation process of the present invention utilizing a porous inorganic material absorber in a continuous reactor wherein the absorber circulates throughout the reactor.

Referring now to FIG. 2, a schematic diagram is shown of a continuous series of reactor chambers, which are suitable for continuously preparing a sulfonated product. Porous inorganic material absorber 112 circulates through the reactor chambers. The continuous sulfonation method of this embodiment of the invention includes the steps as described hereinbelow.

II. Method for Continuous Sulfonation

The continuous method for preparing a sulfonated compound includes contacting a porous inorganic material absorber 112 with a compound to be sulfonated 114 and is performed in a first chamber 120 of the continuous sulfonation reactor. As with the above described embodiment of the batch method, the compound to be sulfonated 114 is applied in liquid form to an absorber 112 to form an adsorbate 116. The adsorbate is preferably kept in suspension by circulating air, thereby maintaining the adsorbate in a fluidized state. The adsorbate 116 is kept in continuous motion or else it falls into a separate second chamber 130 where the adsorbate is reacted with a sulfonating gas mixture to form the sulfonated product. Preferably, the sulfonating gas mixture includes $SO_3$ gas and a gas inert to reaction with the $SO_3$ gas.

The adsorbate 116 containing the sulfonated product is cooled by cooling the circulating air which keeps the adsorbate in suspension. The circulating air is cooled in cooling chamber 140 and recirculated. The adsorbate is preferably cooled to a temperature of about 20° C. The fluidized adsorbate is then moved or freely falls into a third compartment 150, where excess sulfonating gas is removed by contacting the sulfonated product with dry air at temperatures up to about 80° C. The excess sulfonating gas is recycled for future sulfonation reactions in a sulfonation recycler 160 for future sulfonation reactions. If $SO_3$ is in the sulfonating gas mixture, the $SO_3$ entering the sulfonation recycler is preferably contacted with oleum to increase the concentration of $SO_3$. By using the recycler, a stable concentration of $SO_3$ is continuously regenerated for use in subsequent sulfonation reactions.

During the sulfonation process, acids which were formed on the sulfonated product may be neutralized by the addition of a neutralizing agent, preferably including hydroxides, carbonates, acetates and salts of Li, Na, K, Ca, Ba, Zn, Mg, Al and other similar metals. Another method for neutralizing the acids includes contacting the sulfonated product with a mixture of $NH_3$ gas and inert gas in a fourth compartment 170. Next the sulfonated product is moved into water extractor 180, and the sulfonated product is removed by water extraction. The exiting water solution contains the sulfonated product. The absorber is then introduced into dryer 190, where it is dried at a temperature of about 150° C. so that it may be reused in future sulfonation processes.

The porous inorganic material absorber is preferably a porous clay which may comprise magnesium silicate, calcium silicate, or any water insoluble silicate. The preferred absorber is a granular porous silicate clay. The clay is preferably a fired clay which is heated to temperatures of from about 500° to about 1000° C. Upon heating, the clay partially fuses, causing it to sinter and lose bonded water. The clay is a porous glassy mass which can easily be broken and sieved, yielding uniformly sized porous sintered clay. Preferably the clay has an air porosity of about 40±20 percent with a particle size of about 0.01-2.0 mm. Other potentially useful porous absorbers are aluminum oxides and $TiO_2$.

As in the batch sulfonation method described above, the compounds to be sulfonated may also be selected from the group consisting of hydrocarbons, aromatic hydrocarbons, alkylated aromatic hydrocarbons, alkylated diphenyloxides, alkanols, amines, imines, polystyrene and other polymers. The compound to be sulfonated is utilized in an amount between about 5 and about 60 percent by weight of the total Weight of the resulting adsorbate. Preferably the compound to be sulfonated is utilized in an amount between about 20 and about 30 percent by weight of the total weight of the adsorbate.

The compound to be sulfonated is reacted with a sulfonating gas mixture which preferably includes $SO_3$ gas and a gas which is inert to the $SO_3$ gas. The $SO_3$ gas is preferably obtained from a sulfonator-recycler as described hereinabove. The inert gas may be any gas which does not react with $SO_3$. Acceptable inert gases include dry air, nitrogen, argon, $CO_2$ and $SO_2$. The $SO_3$ content of the sulfonating gas mixture is between about 10 ppm up to about 30 percent by volume based on total volume of the air/gas mixture. Preferably, the $SO_3$ content of the mixture is between about 5 and about 30 percent by volume based on total volume of the air/gas mixture. Most preferably, the $SO_3$ content of the mixture is between about 5 and about 10 percent by volume based on total volume of the air/gas mixture.

The sulfonating reaction is most effectively carried out when the clay is fluidized to permit greater surface contact with the sulfonating gas mixture and the adsorbate. Fluidization may be achieved mechanically by using stirring blades, a tower through which the clay falls, a rotating slant tube, and various vibration devices. Alternatively, the sulfonation gas mixture itself may be used to fluidize the clay. When this method is used, lower levels of $SO_3$ gas may be utilized in the reactor.

The porous inorganic material absorber or clay containing the compound to be sulfonated is reacted with the sulfonating gas mixture to form a sulfonated product which remains on the absorber. After formation of the sulfonated product, any excess $SO_3$ is removed from the product in third compartment 150 by contacting the product with dry, slightly warm air. The air may be heated to a temperature of up to about 80° C. When small particle size clay is utilized, there appears to be little or no unsulfonated compound.

In the continuous process of sulfonation, certain sulfur-containing acids may form on the absorber. Likewise in the batch method, these acids may be neutralized with a neutralizing agent, such as an aqueous base solution including the hydroxides, carbonates, acetates or salts, as described hereinabove. When contacted with the aqueous base solution, the sulfonated product dissolves into the base and neutralization of the acid and water extraction of the sulfonated product occur simultaneously. This process is well known in the art.

Alternatively, again, neutralization may be accomplished with a neutralizing gas mixture, such as $NH_3$ gas. Also, other neutralizing gas mixtures may be utilized which include $NH_3$ in combination with a gas which is inert to $NH_3$. Such insert gases may include air, nitrogen and argon. In that case, $NH_3$ is utilized in an amount between about 5 and about 95 percent by volume based on total volume of the neutralizing gas mixture. Preferably the $NH_3$ gas is present in an amount between about 5 and about 10 percent by volume based on total volume of the neutralizing gas mixture. Following neutralization by using a neutralizing gas mixture including $NH_3$ gas, excess $NH_3$ is removed by heating the product to a temperature of up to about 80° C., and followed by air flushing. The sulfonated product is then removed from the porous absorber, preferably by water extraction, resulting in a concentrated solution of sulfonated product in water. A substantially water-free sulfonated product may be obtained by simple distillation.

Following removal of the sulfonated product, the wet porous inorganic absorber is then dried by subjecting it to a temperature of about 150° C. to remove traces of water, thereby restoring the absorber for use in future sulfonation processes.

A sulfonated compound having less than about 1.0 percent by weight of inorganic salts may be prepared by a method which first includes contacting a porous inorganic material absorber with a compound to be sulfonated to form an adsorbate. The compound to be sulfonated may preferably include alkylated aromatic hydrocarbons, wherein the compound to be sulfonated is between about 20 and about 30 percent by weight of the total weight of the resulting adsorbate.

Thereafter, reacting the adsorbate with a sulfonating gas mixture, including $SO_3$ gas and a gas inert to reaction with $SO_3$ yields a sulfonated product. The $SO_3$ is preferably present in an amount between about 5 and about 30 percent by volume based on total volume of sulfonating gas mixture. Removal of excess $SO_3$ gas after the adsorbate is reacted with the $SO_3$ gas mixture is then effected by contacting the absorber containing sulfonated product with dry air at temperatures of up to about 80° C. The excess $SO_3$ may be recycled for use in subsequent sulfonation reactions.

Acids which are formed on the adsorbate may be neutralized and extracted by admixing with a neutralizing agent selected from the group consisting of aqueous solutions of the hydroxides, carbonates, acetates and salts of Li, Na, K, Ca, Ba, Zn, Mg, Al, $NH_4$ and similar metals. After neutralization and extraction of the sulfonated product the absorber is dried for reuse by heating the absorber with hot air to a temperature of about 150° C. The resultant sulfonated alkylated aromatic compound contains inorganic salts present in an amount of less than about 1.0 percent by weight based on total compound weight, and in many cases the inorganic salts are present in an amount of less than about 0.1 percent by weight based on the total weight of the sulfonated compound. The preferred sulfonated product is a sulfonated alkyl diphenyl oxide.

Thus, there is provided in accordance with the present invention a sulfonation method which utilizes a porous inorganic absorber which is reusable in the sulfonation process and produces little or no byproducts and waste products. The sulfonation process results in a sulfonated product generally having less than about 0.1 percent inorganic salts and no more than about 1.0 percent inorganic salts based on total weight of the sulfonated product. The process uses recycled $SO_3$ resulting in a more efficient, environmentally safe, cost effective process.

While the invention has been described in terms of several specific embodiments, it must be appreciated that other embodiments could readily be adapted by one skilled in the art. Accordingly, the scope of the invention is to be limited only by the following claims.

What is claimed is:

1. A method for preparing a sulfonated compound on a porous inorganic material carrier-absorber which produces minimal or no waste products, comprising:
   (a) contacting a porous inorganic material absorber with a compound to be sulfonated selected from the group consisting of hydrocarbons, aromatic hydrocarbons, alkylated aromatic hydrocarbons, alkanols, amines, imines, and polystyrene to from an adsorbate;
   (b) reacting the adsorbate with a sulfonating gas containing $SO_3$ gas in order to from a sulfonated product;
   (c) neutralizing the sulfonated product; and
   (d) removing the sulfonated product from the inorganic material adsorber.

2. The method of claim 1, wherein the compound to be sulfonated is an alkylated diphenyloxide.

3. The method of claim 1, wherein the step of contacting a porous inorganic material with a compound to be sulfonated is accomplished by using the compound to be sulfonated in an amount between about 5 and about 60 percent by weight of the total weight of the resulting adsorbate.

4. The method of claim 1, wherein the step of contacting a porous inorganic material with a compound to be sulfonated is accomplished by using the compound to be sulfonated in an amount between about 20 and about 30 percent by weight of the total weight of the resulting adsorbate.

5. The method of claim 1, wherein the step of contacting a porous inorganic material absorber with a compound to be sulfonated is accomplished by contacting an absorber which is granular porous silicate clay.

6. The method of claim 1, wherein said step of reacting the adsorbate with a sulfonating gas is accomplished by reacting the adsorbate with a gas mixture containing $SO_3$ gas along with a gas which is inert to reaction with the $SO_3$ in order to form a sulfonated product.

7. The method of claim 5, wherein the step of reacting the adsorbate with a sulfonating gas is accomplished by using the granular porous silicate clay in a fluidized state.

8. The method of claim 1, wherein the step of reacting the adsorbate with a sulfonating gas is accomplished by utilizing $SO_3$ gas which is recovered and recycled during the sulfonation process.

9. The method of claim 1, wherein the step of reacting the adsorbate with a sulfonating gas is accomplished by reacting a sulfonating gas having an $SO_3$ content of from about 5 to about 30 percent by volume based on total volume of the sulfonating gas.

10. The method of claim 1, further comprising a step of removing excess $SO_3$ gas after the adsorbate is reacted with the sulfonating gas by contacting the adsorbate with dry air at temperatures of up to about 80° C.

11. The method of claim 1, wherein the step of neutralizing the sulfonated product is accomplished by admixing a neutralizing agent selected from the group consisting of aqueous solutions of the hydroxides, carbonates, acetates and salts of Li, Na, K, Ca, Ba, Zn, Mg and Al with the sulfonated product.

12. The method of claim 1, wherein the step of neutralizing the sulfonated product is accomplished by contacting the sulfonated product with a neutralizing gas mixture of $NH_3$ gas and a gas inert to reaction with $NH_3$, wherein the $NH_3$ gas is present in an amount between about 5 and about 95 percent by volume based on total volume of the neutralizing gas mixture.

13. The method of claim 12, wherein the step of neutralizing the sulfonated product is accomplished by utilizing $NH_3$ gas in an amount between about 5 and about 10 percent by volume based on total volume of the neutralizing gas mixture.

14. The method of claim 12, further comprising a step of removing excess $NH_3$ gas from the neutralized sulfonated product by heating the absorber containing the sulfonated product to a temperature of up to about 80° C. and air flushing.

15. The method of claim 1, further comprising a step of removing the sulfonated product from the porous absorber by water extraction.

16. The method of claim 1, further comprising a step of distilling water from the sulfonated product to achieve a substantially water-free product.

17. The method of claim 1, further comprising the step of drying the absorber reuse by heating the absorber to a temperature of about 150° C.

* * * * *